US010111427B2

(12) United States Patent
Sawant et al.

(10) Patent No.: US 10,111,427 B2
(45) Date of Patent: Oct. 30, 2018

(54) FORMULATION FOR IMPROVING THE YIELD AND QUALITY OF FIBER IN COTTON PLANTS

(71) Applicant: Council of Scientific & Industrial Research, New Delhi (IN)

(72) Inventors: Samir Viswanath Sawant, Lucknow (IN); Sunil Kumar Singh, Lucknow (IN); Babita Singh, Lucknow (IN); Parthasarathi Bhattacharya, Hyderabad (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 15/547,370

(22) PCT Filed: Jan. 28, 2016

(86) PCT No.: PCT/IN2016/050027
§ 371 (c)(1),
(2) Date: Jul. 28, 2017

(87) PCT Pub. No.: WO2016/120889
PCT Pub. Date: Aug. 4, 2016

(65) Prior Publication Data
US 2018/0027811 A1 Feb. 1, 2018

(30) Foreign Application Priority Data
Jan. 28, 2015 (IN) .............................. 231/DEL/2015

(51) Int. Cl.
*A01N 37/40* (2006.01)
*A01N 37/10* (2006.01)
*A01N 45/00* (2006.01)
(52) U.S. Cl.
CPC ............. *A01N 37/40* (2013.01); *A01N 37/10* (2013.01); *A01N 45/00* (2013.01)
(58) Field of Classification Search
None
See application file for complete search history.

(56) References Cited

U.S. PATENT DOCUMENTS

| 4,565,875 | A | 1/1986 | Cavendar |
| 4,581,057 | A | 4/1986 | Noodén |
| 5,004,863 | A | 4/1991 | Umbeck |
| 6,472,588 | B1 | 10/2002 | Haigler et al. |
| 2013/0047505 | A1 | 2/2013 | Ng |

FOREIGN PATENT DOCUMENTS

| CN | 101 913 927 | 12/2010 |
| CN | 103 524 198 | 1/2014 |
| WO | WO-03/090533 | 11/2003 |
| WO | WO-2008/147078 | 12/2008 |
| WO | WO-2013/037955 | 3/2013 |
| WO | WO-2013/121190 | 8/2013 |

OTHER PUBLICATIONS

Hemshekhar et al., Emerging Roles of Anacardic Acid and Its Derivatives: A Pharmacological Overview, Basic & Clinical Pharmacology & Toxicology, 110, 122-132, 2011.*
Jenkins et al, "Genetic Effects of Thirteen *Gossypium barbadense* L. Chromosome Substitution Lines in Toperosses with Upland C . . . ", Crop Science, vol. 47, pp. 561-572, (2007).
Beasley et al., "The Effects of Plant Growth Substances on in Vitro Fiber Development from Fertilized Cotton Ovules," Ame. J. of Botany, vol. 60, No. 2, pp. 130-139 (1973).
International Search Report for PCT/IN2016/050027 dated May 3, 2016.
Written Opinion for PCT/IN2016/050027 dated May 3, 2016.
Percival et al., "The Influence of Plant Growth Regulators on Root and Shoot Growth of Containerized Trees Following . . . ," J.of Horticultural Sci & Bio, pp. 353-359, (1998).
Lee et al., "Xyloglucan Endotransglycosylase/Hydrolase Genes in Cotton and Their Role in Fiber Elongation," Planta, pp. 1191-1205 (2010).
Sun et al., "Brassinosteroid Regulates Fiber Development on Cultured Cotton Ovules," Plant Cell Physiol. vol. 46, No. 8, pp. 1384-1391 (2005).
Pu et al., "The R2T3 MYB Transcription Factor GhMYB109 is Required for Cotton Fiber Development," Genetics, vol. 180, pp. 811-820, (2008).
Zhang et al. "Variations and Transmissions of QTL Alleles for Yield and Fiber Qualities in Upland Cotton Cultivars Developed in China" PLOS One, V-8, 1-2, pp. 1-12 (2013).
Gialvalis et al., "Plant Hormones Alter Fiber Initiation in Unfertilized, Cultured Ovules of Gossypium Hirsutum," Journal of Cotton Science, vol. 5, pp. 252-258 (2001).
Pasapula et al., "Expression of an Arabidopsis Vacuolar H+-Pyrophosphatase Gene (AVP1) in Cotton Improves Drought- . . . " Plant Biotechnology Journal, vol. 9, pp. 89-99 (2011).

(Continued)

*Primary Examiner* — Alton N Pryor
(74) *Attorney, Agent, or Firm* — Nixon Peabody LLP; Jeffrey L. Costellia

(57) ABSTRACT

The present invention relates to a novel formulation, comprising Anacardic acid or its derivatives and phytohormones (1-NAA and GA3), which promotes the increase in fiber yield and improvement in fiber quality. The in-vitro ovule culture assay was used to check the effect of formulation on initiation and development of cotton fiber. Increased initiation and length of cotton fibers was observed in the cultured ovules treated with the formulation which were validated by biochemical assays. The formulation was applied directly onto the at least 70 plants of *Gossypium hirsutum* genotypes in three replicates with control plants treated with phytohormones only. The formulation was applied by spraying on buds, flowers and bolls. The treated plants show significant increase in boll weight, fiber length, fineness and fiber strength. Thus, the formulation may serve as an important plant growth stimulator leading to the increase in fiber yield and improvement in fiber quality in cotton plants.

11 Claims, 9 Drawing Sheets

(56) References Cited

OTHER PUBLICATIONS

Meredith, "Influence on Cotton Breeding on Yield and Fiber Quality Problems," Cotton Incorporated Proceedings, 10 pages, (2005).
Singh et al., "Breeding Hybrid Cotton", Cevtral Institute for Cotton Research Nagur, CICR Technical Bulletin No. 14, pp. 1-17, (2000).
Haigler et al., "Biotechnological Improvements of Cotton Fibre Maturity," Physiologia Plantarium, vol. 124, pp. 285-294 (2005).
Bhardwaj et al., "Influence of IAA and GA3 in Fibre Properties and Growth of Cotton Bolls," Indian J. Agric. Sci., vol. 41, No. 6, pp. 524-527 (1971).
Singh et al., "Effect of Growth Regulators on Early Fibre Development in Cotton," Indian Journal of Experimental Biology, vol. 13, No. 4, pp. 411-412 (1975).
Lewis, "The Proceedings of Cotton Fiber Cellulose: Structure Function and Utilization Conference", Cotton, Inc., pp. 4-18 (1992).
Harris, "Weather, Tobacco Budworms Hurt 2000 Variety Trial Yields", Cotton Farming, p. 26, (2001).
Baert et al., "Influence of Growth Hormones Upon Fiber Development," Cellulae, col. 71, pp. 55-63, (1975).
Dhindsa et al., "Effects of Abscisic Acid on In Vitro Growth of Cotton Fiber", Planta (Berl.), vol. 130, pp. 197-201 (1976).

\* cited by examiner (** Significant with p-value 0.01)

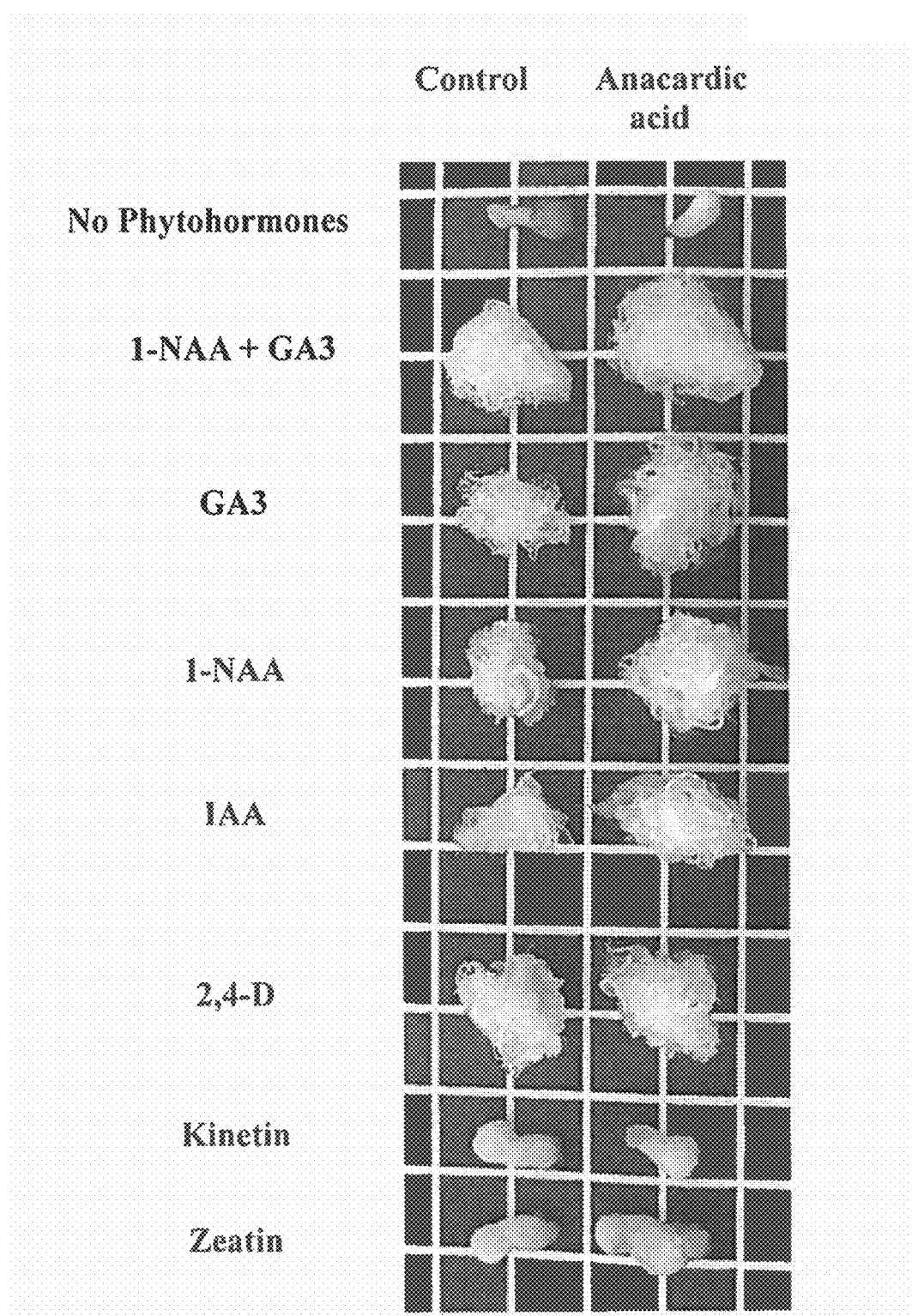
Figure 8: cotton ovules cultured with different phytohormones with and without Anacardic acid (control) at 12 DPA stage.

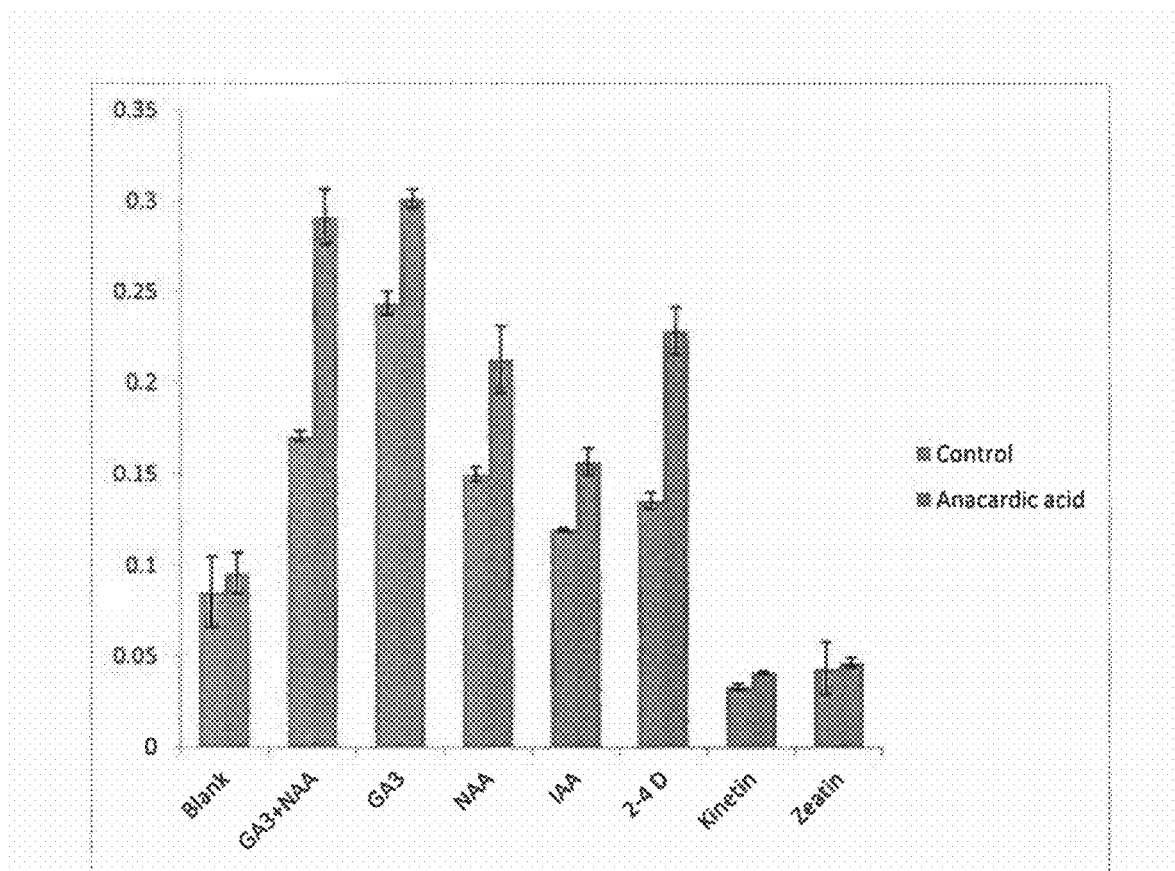
Figure 9: Lignin quantification of 12 DPA cotton ovules cultured with different phytohormones with and without Anacardic acid (control).

FORMULATION FOR IMPROVING THE YIELD AND QUALITY OF FIBER IN COTTON PLANTS

FIELD OF INVENTION

The present invention is related to a novel formulation comprising phytohormones and phenolic lipids in a specific combination which is biologically effective. This novel formulation, when applied to the cotton plants, increases the yield and quality of fiber by increasing boll weight, fiber length, fineness and strength of cotton fiber.

BACKGROUND OF THE INVENTION

Cotton is an important crop which is cultivated usually for fiber production. Fiber is collected from cotton bolls which are formed on cotton plant and have different application including textile and medical. Yield per plant is the most important attribute for the cotton growers besides fibre quality which leads to increasing acreage and market price. Yield of fiber in cotton plants depends on a number of internal and external characteristics (Harris, 2001. Cotton Farm. 45:26) including environmental, nutritional and hormonal conditions, expression of important proteins, as well as standard agricultural practices. Fiber yield is a combinatorial effect of fiber length, number of fibers per boll, and number of bolls per plant. Deviation in any of these parameters affects the yield of fiber in cotton (Haigler et al., 2005. Physiologia plantarum, 124(3), 285-294). Quality of cotton fiber is characterized by various factors including its length, fineness and strength.

Several approaches have been followed to improve the yield of cotton fiber on cotton plants (Lewis, 1992. The proceedings of cotton fiber cellulose: Structure function and utilization conference. p. 4-18. Savannah Ga. 28-31 Oct. 1992. Cotton Inc., Raleigh, N.C.) and these can be widely distributed in these classes on the basis of approach followed:

a. Breeding Approach

This is the most common approach for variety improvement. Conventional as well as marker based plant breeding approaches have been followed for fiber yield improvement in cotton (Meredith Jr, W R. 2005. Influence of cotton breeding on yield and fiber quality problems. Cotton Incorporated Proceedings. Jun. 6-8, 2005, Memphis, Tenn.). In India, H4 was the first cotton hybrids, which was released in 1970 and another hybrid Varalaxmi was released in 1972 (Singh et al., Breeding hybrid cotton, CICR technical bulletin No. 14, CICR, India).

Worldwide, several QTLs for yield and quality traits of cotton fiber have been identified and being used in breeding programme (Zhang et al., 2013. Variations and transmission of QTL alleles for yield and fiber qualities in Upland cotton cultivars developed in China. PloS one, 8(2), e57220; Jenkins et al., 2007. Genetic effects of thirteen *Gossypizon barbadense* L. chromosome substitution lines in toperosses with upland cotton cultivars: II. Fiber quality traits. Crop Science-Madison-47.2: 561). Although breeding approach in cotton has been a reliable method, the amount of time needed for development of an improved variety and limited variability available in cotton genotypes make this approach rather difficult.

b. Transgenic Approach

This includes variety improvement by gene recombination technique. Several attempts have been made to functionally characterize different genes and their introduction to the plants for expression/improvement of a desired trait thereon. Different genes encoding yield related proteins have been introduced to the cotton plants (Umbeck P F. Genetic engineering of cotton plants and lines, U.S. Pat. No. 5,004,863. 17 Oct. 2000). For example, method for increasing the quality of cotton fiber produced from a cotton plant by transformation with a DNA encoding sucrose phosphate synthase has been developed (Haigler & Holaday. 2002. U.S. Pat. No. 6,472,588. Washington, D.C.: U.S. Patent and Trademark Office). Similarly, expression of an *Arabidopsis* vacuolar H+-pyrophosphatase gene (AVP1) in cotton was also reported to increase fibre yield in the field conditions (Pasapula et al. 2011. Plant biotechnology journal 9.1 (2011): 88-99). Genes associated with fiber initiation and elongation has been incorporated for improving fiber characteristics and per plant yield in cotton (Pu et al. 2008. Genetics, 180.2, 811-820; and Lee et al., 2010. Planta 232.5, 11911205). But, as the fiber development in cotton is not fully elucidated and all the factors contributing fiber development and yield are not yet known, significant improvement in fiber yield has not been achieved by this approach.

c. Chemical Approach

This method majorly includes the application of plant hormones and growth supplements/stimulants directly on to the plant parts or in the soil. Plant hormones like auxin, gibberellin, cytokinin and ethylene are widely used to agricultural crops and horticultural products for alteration in different plant characteristics.

Several reports have been made citing the effect of these hormones on fiber quality and its yield. Auxin and gibberellin have been reported to promote fiber elongation by Bhardwaj and Sharma, 1971 (Ind J Agnc S ci. 41: 524-527), Singh and Singh, 1975 (Ind. J. Exp. Bioi. 13:411-412), Baert et al., 1975 (La Cellule, 71:55-63) and Gialvalis and Seagull, 2001 (The Journal of Cotton Science, 5:252-258). While, Dhindsa et al. (Planta (1976) 130:197-201) reported the inhibitory effect of abscisic acid on fiber elongation.

Similarly, brassinosteroids have been reported to promote fiber development in cotton ovule culture (Beasley and Ting, 1973. Amer J Bot, 60: 130-139; Sun et al., 2005. Plant and Cell Physiol. 46: 1384-1391). Gialvalis and Seagull, 2001 (The Journal of Cotton Science, 5:252258) confirmed that exogenous application of hormones for yield improvement in cotton is time dependent (pre or post anthesis). Acylsulfonamides are also reported to improve yield in cotton and other plants (Bayer Intellectual Property GMBH et al., Use of acylsulfonamides for improving plant yield. 20 Sep. 2013, U.S. Patent Application. PCT/EP2012/068096). Similarly, Abscisic acid (Nooden, Larry D. "Abscisic acid containing foliar fertilizers and method of using same to enhance crop yields". U.S. Pat. No. 4,581,057. 8 Apr. 1986) and Imidazole (Cavender, Patricia L. "Imidazole plant growth regulators". U.S. Pat. No. 4,565,875. 21 Jan. 1986) was also reported to enhance yield in cotton and other crop plants. Some commercial growth stimulants are also available in the market for crop plants.

Limitation in Prior Art

Although there are various growth stimulating formulations are available, their effect has not been consistent and fully confirmed to prove them effective for agricultural use. Some Phytohormones have also been used exogenously for plant yield improvement, but their effect is time dependent (Gialvalis and Seagull, 2001. The Journal of Cotton Science, 5:252258) and thus cannot be used as such for cotton plants, where flowering is largely asynchronous. Secondly, the quantity of the phytohormones needed for the effect is not well established. Hence there is a need for an effective formulation which can be used to increase yield and quality of cotton fiber and can be directly applied on the cotton plants. In the present invention this problem has been resolved.

OBJECTS OF THE INVENTION

1) The main objective of the invention is to increase the fiber yield and improvement in quality of cotton fiber which may be defined as fiber length, fineness and strength.
2) Another objective of the present invention is to identify a growth stimulating formulation, which can be applied exogenously to the cotton plant to increase its yield.
3) Another objective of the present invention is to identify a growth stimulating formulation, which is preferably of plant origin and can be applied directly to the cotton plant to increase its yield.
4) Yet another objective of this invention is to identify the phytohormones, which can be mixed in an appropriate concentration with other compounds and can be applied directly to the plant to increase its yield.
5) Yet another objective of this invention is to identify a compound to make a formulation with phytohormones, which can be applied directly to the cotton plants to increase fiber yield.
6) Yet another objective of this invention is to establish a suitable concentration of auxin and gibberelic acid along with the additive chemical, which can be applied directly to the cotton plant to increase fiber yield.
7) Yet another objective of this invention is to establish a suitable concentration of Anacardic acid or its derivatives as compound mentioned in objectives 4 and 5, which can mixed with the phytohormones and this formulation can be applied directly to the cotton plant to increase fiber yield.
8) Yet another objective of this invention is to establish a method of using the formulation for increasing the fiber content of the cotton plant.

SUMMARY OF THE INVENTION

The present invention relates to a plant growth stimulating formulation, for improving fiber yield and quality of the plant, comprising a solution of Anacardic acid or its other derivatives at a concentration ranging from 2-20 µm, along with Phytohormone ingredient selected from 1-Naphthaleneacetic acid (1-NAA), Indoleaceteic acid (IAA), 4-chloroindole-3-acetic acid, phenylacetic acid, indole-3-butyric acid (IBA) and Gibberellic Acid either individually or in combination.

In one embodiment of the invention, the solvent used for Anacardic Acid is selected from dimethyl sulfoxide (DMSO), dimethyl formamide (DMFO), ethanol methanol, dichloromethane, ether, petroleum ether and ethyl acetate in a biologically effective concentration. In one of the preferred embodiment the solvent used for Anacardic acid or its derivatives is dimethyl sulfoxide (DMSO).

In another embodiment of the invention, the concentration of 1-NAA used in the formulation is in the range of 2 to 20 µM.

In yet another embodiment, the concentration of GA3 or gibberelic acid used in the formulation is ranging from 0.1 to 5 µM.

In one embodiment of the invention, the formulation contains 27.84 mg/litre Anacardic acid, 1.12 mg/litre 1-NAA and 0.173 mg/litre GA3.

In another embodiment of the invention, the formulation is formulated into a liquid, paste, powder or granule composition.

In yet another embodiment the present invention provides a method of application of the plant growth stimulating formulation for the improvement in yield and quality of cotton fiber.

In yet another embodiment, the application of the formulation to cotton plants increases boll weight approximately by 1.8% to 29.39%.

In yet another embodiment, the application of the formulation to cotton plants increases fiber length approximately by 0.57% to 11.09%.

In one embodiment, the present invention provides a method of enhancing the yield and quality of cotton fiber using the formulation comprising the steps of:
(a) spraying of the formulation on the shoot or buds, flowers and bolls of the cotton plant; alternatively, top dressing of the formulation on the cotton plants if the formulation is in powder or granule form;
(b) repeating the process of for 3-5 times;
(c) setting the desired yield on maturity of seeds of the sprayed flower, buds and bolls In one embodiment of the invention, different concentrations of ingredients of the formulation of the invention were made.

In another embodiment of the invention, formulation was initially tested by using it in ovule culture media for culturing cotton ovules.

In yet another embodiment, most effective formulation was identified and used for ovule culture.

In yet another embodiment, effect of the formulation was quantified in-vitro, using ovule culture assay.

In yet another embodiment, most effective formulation was tested in field for desired properties.

In yet another embodiment, effect of application of the formulation of invention was quantified on yield and quality of cotton fiber.

Further, the present invention relates to identification of a plant growth stimulating formulation and method of its direct application on plant for improvement in yield. In a particular embodiment of present invention relates to the method of obtaining significant improvement in plant yield without involving breeding or transgenic approach (by direct/indirect transfer of genetic material). In one embodiment, this invention relates to use of specified formulation for yield improvement on cotton plant but not restricted as it can be used for other plants also for greater yield. Another embodiment of the present invention relates to the use of formulated combination for quality improvement of cotton fiber which can be represented by length, fineness and/or strength of fiber.

BRIEF DESCRIPTION OF DRAWINGS

FIG. 8 illustrates cotton ovules cultured with different phytohormones with and without Anacardic acid (control) at 12 DPA stage.

FIG. 9 illustrates Lignin qualifications of 12 DPA cotton cultured with different phytohormones with and without Anacardic acid (control).

DETAILED DESCRIPTION OF THE INVENTION

Figure 1:
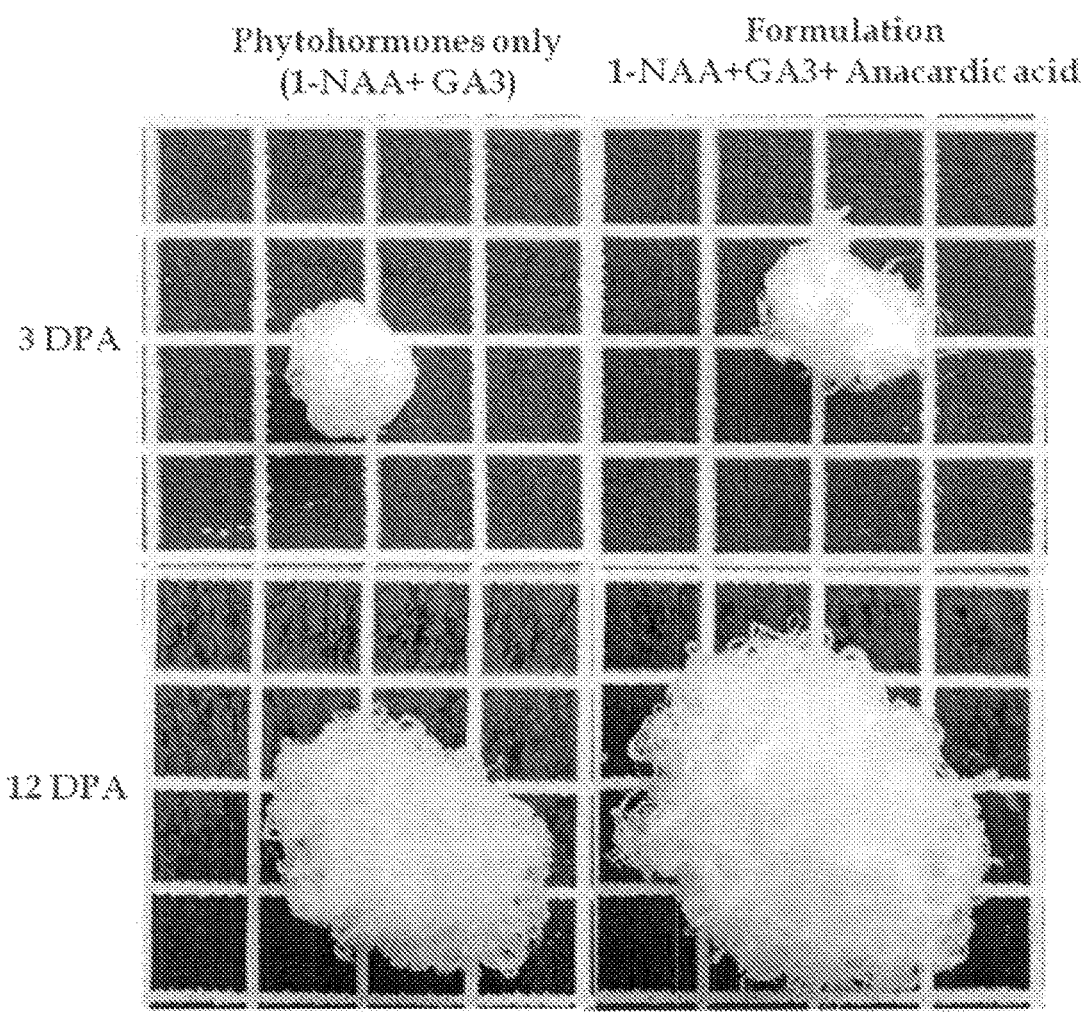
FIG. 1 illustrates the in-vitro ovule culture assay after fiber initiation (3 DPA) and at fiber elongation (12 DPA) stage using the formulation wherein Anacardic acid (8 µM), 1-NAA (5 µM) and GA3 (0.5 µM) are present in culture media (½ MSL with 2% sucrose) in comparison to control wherein only phytohormones are used. Ovules were excised from cotton bud at −3 DPA for initiation stage and at 0 DPA for elongation stage (addition of Anacardic acid at 3 DPA) and cultured in media at 32° C. Photographs are taken at 3 DPA for initiation stage and at 12 DPA for elongation stage. Cotton ovules cultured with the formulation (1-NAA+GA3+Anacardic acid) in culture media show higher number of initiating fibers and better growth in comparison to control ovules (only phytohormones treated).

Various compounds act as 'plant growth stimulants' and increase yield of the plant, directly or indirectly. The term "plant growth stimulants" relate to a variety of compounds either solely or in combinations which stimulate various plant responses to improve some plant characteristics. The plant growth stimulants are different from those having inhibitory or toxic effects on plant growth or yield, like, pesticides and sometimes referred as 'plant growth regulators'. The present invention describes use of a specific formulation containing certain chemicals present in a concentration, which is neither inhibitory to plant growth nor phytotoxic in nature, but promotes its growth in such a way that final yield increases significantly.

Plant growth stimulants are needed to improve plant growth and its condition so that it drives yield improvement in treated plants significantly than non-treated plants. Several plant growth stimulants have been reported and some are in commercial production. Plant growth stimulants are usually effective in very less concentration and may affect different cellular processes like cell differentiation, cell division and/or elongation. These may contain natural chemicals like plant hormones (auxins, gibberellins, cytokinins, ethylenes, abcissic acid and salicylic acid) and fatty acid derivatives (jasmonic acids) or can be synthetic chemicals and combinations.

Cotton is the most important fiber crop in the world. Cotton fibers are seed trichomes which are developed from epidermal cells of ovule. The development of cotton fiber is a complex process which can be divided into 4 overlapping stages, initiation, elongation, secondary cell wall synthesis and maturation stage. Here, DPA is "Day Post Anthesis" which can be defined as time (in days) after the fertilization or opening of the flower. At the initiation stage (−3 to 5 DPA), a fiber cell is initiated from outer epidermis of the cotton ovule. At the elongation stage (3 to 20 DPA), elongation of fiber cells occurs and they increase in length. At the secondary cell wall synthesis stage (19 to 40 DPA), cellulose is deposited in the fiber cell wall. Similarly, at the maturation stage (40 DPA and above), the fiber cell starts drying and the biological activity of the fiber cell ceases.

A large number of genes contribute to the initiation and elongation of the cotton fiber (Lee et al., 2007. Annals of botany, 100(7), 1391-1401). A growth stimulant may affect the expression of these genes and may stimulate the plant for better yield. The yield of cotton fiber per plant depends upon the number of bolls present on the plant, number of fibers present per boll and length of the fibers. Similarly, quality of the fiber mainly depends upon its length, which is expressed as 50 or 2.5% span length (means n % fibers are larger than the given value), strength, which is expressed as gram per tex, and its fineness, which is expressed as micronaire value (Smith and Coyle, 1997. Crop science, 37(6), 1775-1779).

The present invention relates to a novel formulation, consisting Anacardic acid or its derivatives and plant hormones (1-NAA and GA3) in a biologically effective concentration, which promotes the increase in fiber yield and quality. Plant hormones or phytohormones are chemical signal molecules, present in very low concentration and regulate growth and development of plant. Plant hormones regulate cellular processes as well as formation of different plant organs or structures. A large number of plant hormone related chemical compounds are being synthesized by humans. These compounds are called as plant growth regulators (PGRs). Plant hormones are widely used to improve agronomic performance of various crops, although their mechanism of function in fiber development is largely unclear. Plant hormones, like auxins and gibberelic acid play a vital role in fiber growth and development.

Auxins were the first plant hormones discovered, while the IAA (Indole acetic acid) was the first auxin isolated. Auxins have been shown to play important role in promoting cell division and elongation in plants. There are four naturally occurring (endogenous) auxins, which include Indoleacetic acid (IAA), 4-chloroindole-3-acetic acid, phenylacetic acid and Indole3-butyric acid (IBA). Some synthetic compounds are also available which have auxinic activity. These include 1-naphthaleneacetic acid (1-NAA), 2,4-dichlorophenoxyacetic acid (2,4-D), and 2,4,5-trichlorophenoxyacetic acid (2,4,5-T). Naphthaleneacetic acid (1-NAA) is a synthetic auxin which has been shown to improve fiber length and fineness in cotton when used exogeneously (Bhatt et al., 1972. Changes in lint characters of cotton varieties by growth regulators. Cotton Grow Rev. 49:160-165). Gibberellic acid (also called as GA or GA3) is a plant hormone which promotes growth and elongation of cells. Exogenous application of Gibberellic acid has also shown to significantly increase fiber length in cotton (Bhatt and Ramanujam, 1972. Some responses of a short-branch cotton variety to gibberellin. Cotton Grow Rev. 48:136-139). These hormones have also been used in combination to other growth regulators.

Anacardic acids are phenolic lipids found in the shell of the cashew nut (*Anacardium occidentale*). Anacardic acid is a mixture of several closely related organic compounds, consisting of a salicylic acid substituted with an alkyl chain (saturated or unsaturated) with 15 or 17 carbon atoms. At least 21 derivative of Anacardic acid has been reported (Hemshekhar et al., 2011. Basic & Clinical Pharmacology & Toxicology, 110, 122-132). It is the main component of cashew nutshell liquid (CNSL) which is widely used in the chemical industry for the production of cardanol. Till date, agronomic use of Anacardic acid or its derivatives is not known.

In the present invention, Anacardic acid may be dissolved in solvents selected from Dimethyl Sulfoxide (DMSO), Dimethyl formamide (DMFO), ethanol methanol, dichloromethane, ether, petroleum ether and ethyl acetate in a suitable concentration and mixed with 1Naphthaleneacetic Acid (1-NAA) and Gibberellic acid (GA3). For standardization of appropriate concentrations of phytohormones and Anacardic acid for better yield and quality of fiber, the formulation and its components were first tested on cultured ovules. Different concentrations of 1-NAA (1, 5, 10 and 20 μM) and GA3 (0.1, 0.5, 1 and 5 μM) were tested in ovule culture media and established that fiber growth was better at 5 μM 1-NAA and 0.5 μM GA3. Similarly, different concentrations of Anacardic acid (2, 4, 8 and 10 μM) were also used and established that fiber growth was better at 8 μM Anacardic acid in media in comparison to other concentrations.

Formulation was diluted with modified ½ MSL (Murasighe Skoog Liquid) media having 2% sucrose for a final concentration of Anacardic acid to 8 μM, 1-NAA to 5 μM and GA3 to 0.5 μM. This formulation was then used to culture cotton, ovules excised at −3 DPA (Day Post Anthesis) to study its effect on fiber initiation and at 0 DPA for fiber elongation. Ovules were examined (at 3 DPA for initiation and at 12 DPA for elongation stage) and photographed (Example 1). Number of fiber initials and fiber length was significantly increased in case of ovules cultured with the formulation (1-NAA, GA3 and Anacardic acid) in comparison to control (1-NAA and GA3 only; FIG. 1). Cotton ovules cultured with the formulation (1-NAA+GA3+ Anacardic acid) in culture media show higher number of initiating fibers and better growth in comparison to control ovules (only phytohormones treated).

The measurement of cotton fiber length or number in cultured ovules is a tedious work as the seed are not fully matured and its length measurement must be done manually. As the ovules bear fibers of varying length, indirect measurement is generally followed. Measurement of relative lignin content is a very good method of comparing alterations in the length and number (yield) of the fibers. Relative lignin content in the fibers collected from 3 cultured ovules for each sample (control and treated samples from initiation (at 3DPA) and elongation (at 12DPA) stage) was quantified using Toluidine Blue staining method (Beasley and Ting, 1974. Effects of plant growth substances on in vitro fiber development from unfertilized cotton ovules. American Journal of Botany. 61: 188-194). Lignin content was found to be higher in case of ovules cultured with formulation (1-NAA+GA3+ Anacardic acid) in comparison to control (Phytohormones only) (Example 2, FIG. 2).

Figure 3:
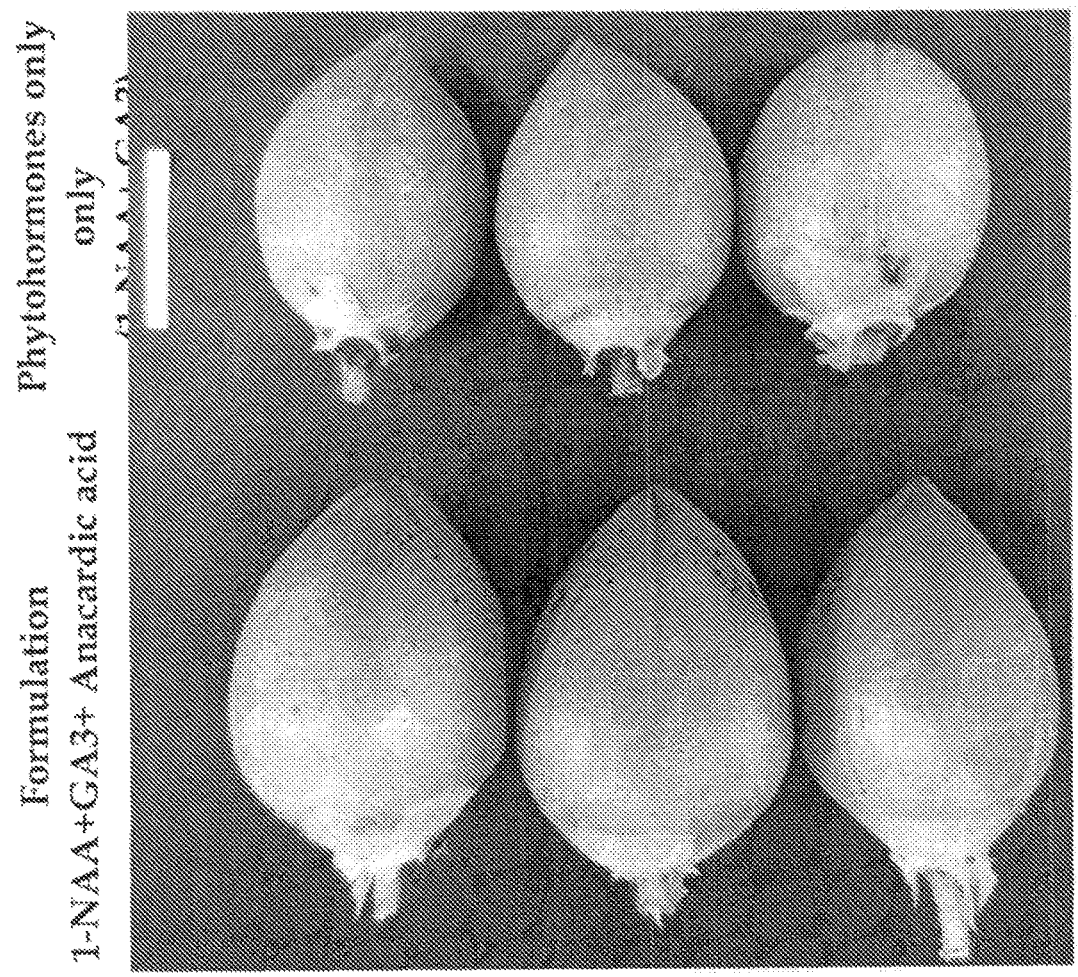
FIG. 3 illustrates difference in boll size in control (Phytohormones treated) and formulation (Phytohormones+ Anacardic acid) treated cotton plants (genotype TSC1098) at 12 DPA. Three bolls were randomly picked from phytohormone (1-NAA+GA3) treated and formulation (1-NAA+ GA3+ Anacardic acid) treated cotton plants (genotype TSC1098) at 12 DPA stage. Cotton bolls from formulation treated plants show increase in size in comparison to bolls from control (phytohormone treated) plants. Length of white bar in the picture is 1 inch.
Figure 4:
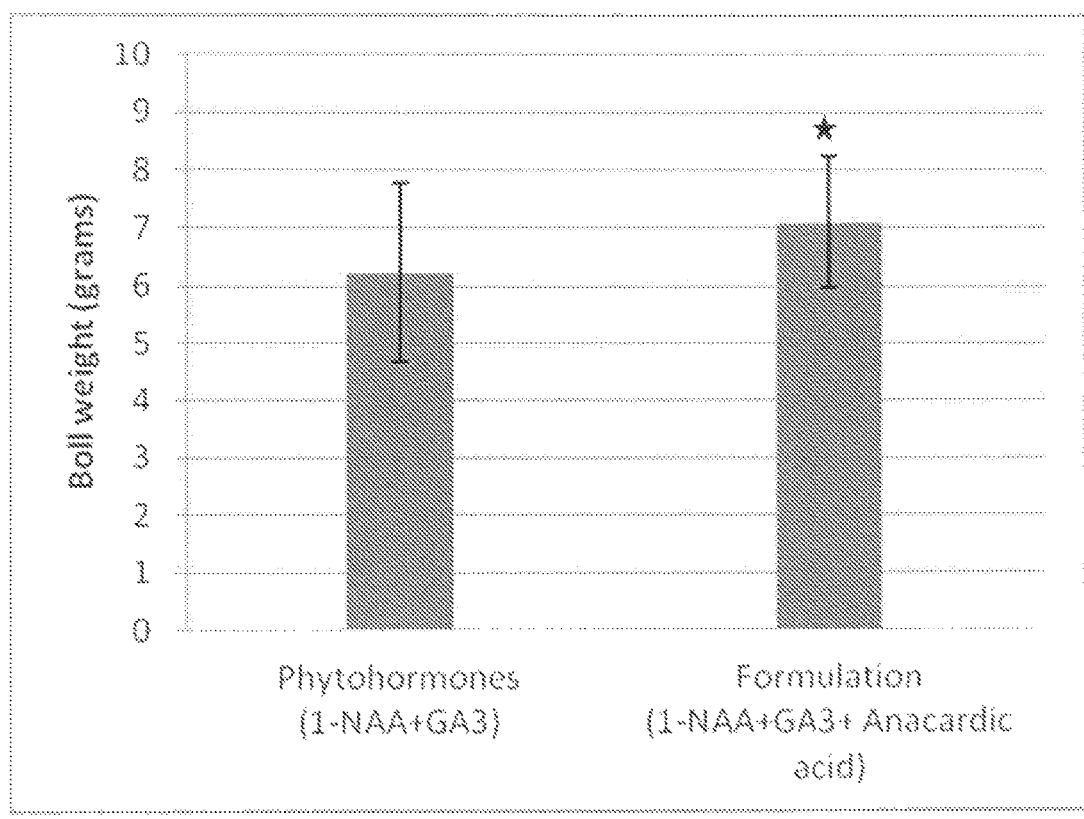
FIG. 4 illustrates boll weight (in grams) of control and treated plants in field condition. For the field trial, *Gossypium hirsutum* genotypes were selected and at least 70 plants each for control and formulation in three replicates were taken for the study under normal agricultural practices. Anacardic acid along with 1-NAA and GA3 mixed with an aqueous base which was directly sprayed on flowering parts of the plants and the treated flowers were tagged accordingly. Mature bolls were collected from control and formulation treated plants (5 plants) in 3 replicates for weight measurement. Cotton bolls treated with the specified formulation (having Anacardic acid) have shown higher weight in comparison to control bolls (treatment without Anacardic acid) indicating higher yield in treated plants.
Figure 5:
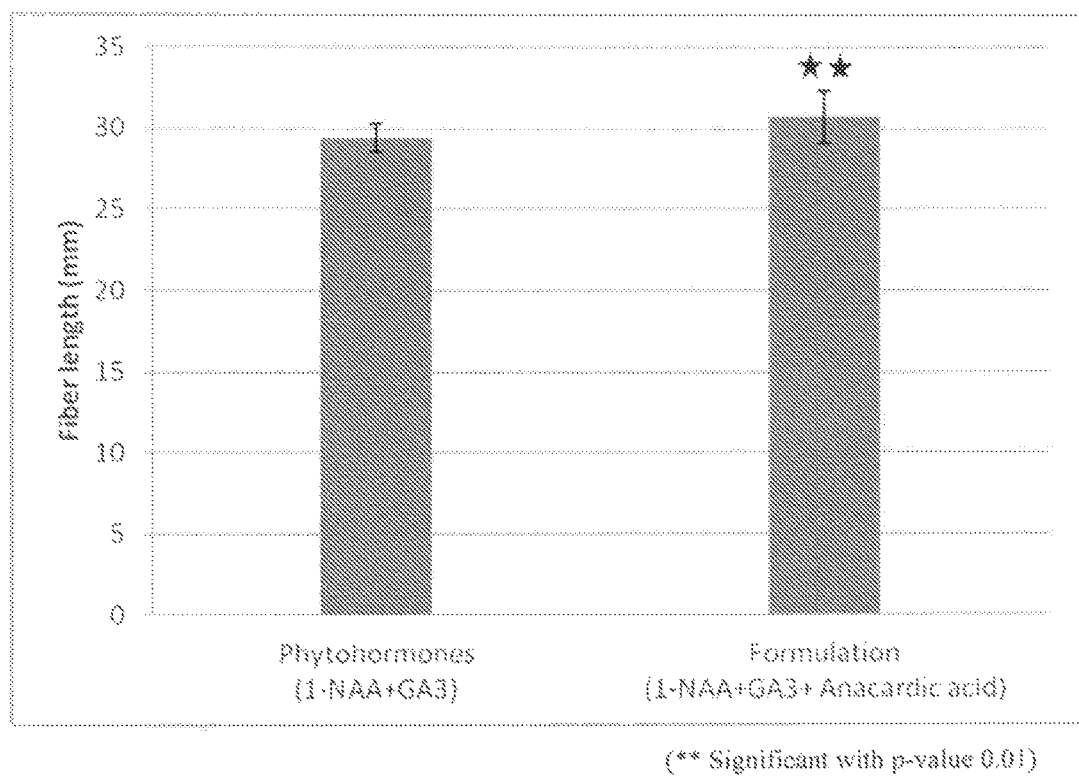
FIG. 5 illustrates length of fibers (expressed as 2.5% span length in millimeter) obtained from cotton plants treated with specified growth stimulating formulation in field condition against fibers from control plants. Matured bolls from treated plants were collected for different fiber measurements against the fibers from control bolls. Cotton fibers from bolls treated with the specified formulation (having Anacardic acid) are greater in length in comparison to fibers from control bolls (treatment without Anacardic acid) indicating greater quality fibers in treated plants.

To test the effect of the formulation on yield and quality of the cotton fiber under normal agricultural practices, field trail was performed. For the field trial, *Gossypium hirsutum* genotypes were selected and at least 70 plants for each treatment with 3 replicates were taken for testing the Anacardic acid and phytohormonal combination for its effect on fiber yield and quality under normal agricultural practices (Example 3). To analyze the difference in boll size at 12 DPA stage, three bolls were randomly picked from phytohormone (1-NAA+GA3) treated and formulation (1-NAA+GA3+ Anacardic acid) treated cotton plants (genotype TSC1098) at 12 DPA stage (Example 3, FIG. 3). Cotton bolls from formulation treated plants show increase in size in comparison to bolls from control (phytohormone treated) plants. Boll weight is a direct measure of fiber yield. Boll weight was calculated by taking an average of 5 bolls from collected randomly from control and formulation treated plants and again an average was calculated for all the 3 replicates (FIG. 4 and Table 2A). Fiber length was calculated from fibers collected from the five plants each of the control and formulation treated in three replicates by HVI testing as 2.5% span length and plotted by taking average (FIG. 5 and Table 2B).

Figure 6:
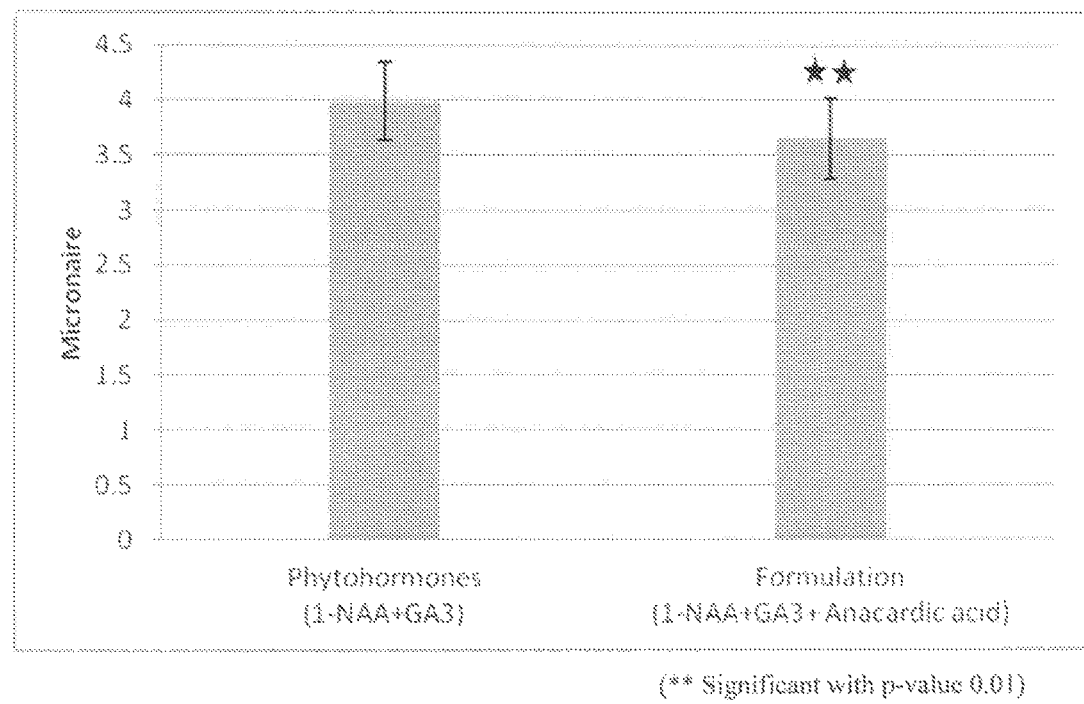
FIG. 6 illustrates fineness of fibers (expressed as micronaire) obtained from cotton plants treated with specified growth stimulating formulation in field condition against fibers from control plants. Fineness is an important parameter of fiber quality and it is desirable to have fine fibers for better fabric texture. Matured bolls from treated plants were collected for different fiber measurements against the fibers from control bolls. Cotton fibers from bolls treated with the specified formulation (having Anacardic acid) are more fine in comparison to fibers from control bolls (treatment without Anacardic acid) indicating greater quality fibers in treated plants.
Figure 7:
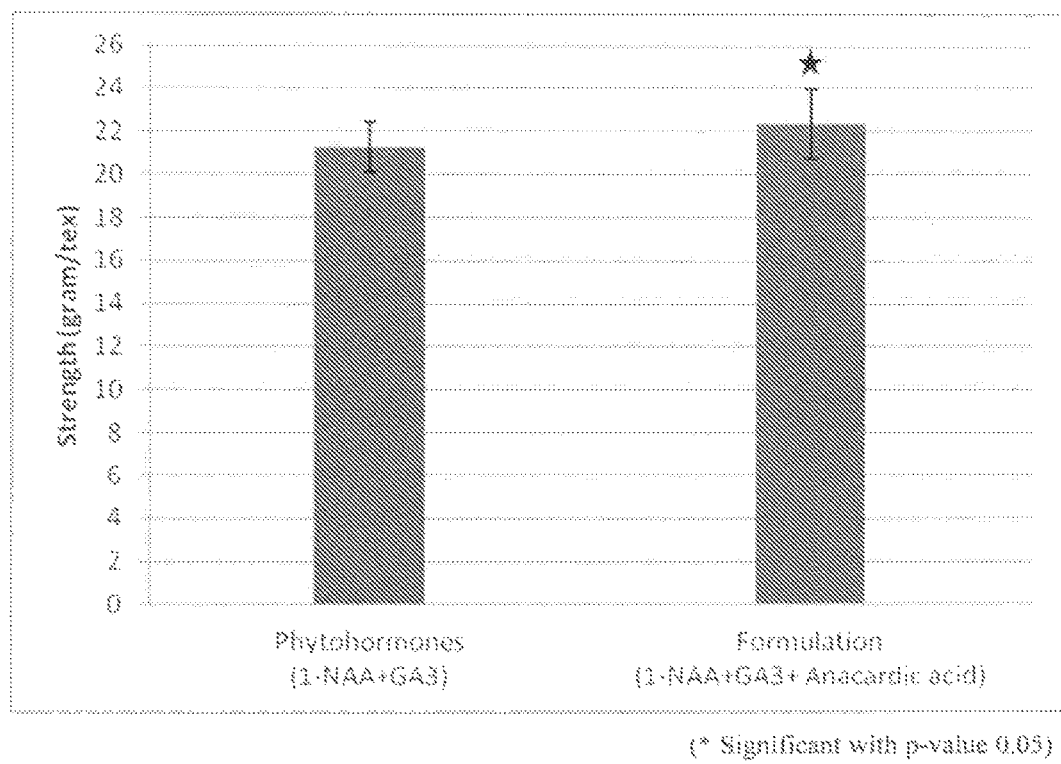
FIG. 7 illustrates strength of fibers (expressed as tenacity in gram/tex) obtained from cotton plants treated with specified growth stimulating formulation in field condition against strength of fibers from control plants. Strength is an important parameter of fiber quality and it is desirable to have stronger fibers. Matured bolls from treated plants were collected for different fiber measurements against the fibers from control bolls. Cotton fibers from bolls treated with the specified formulation (having Anacardic acid) are greater in strength in comparison to fibers from control bolls (treatment without Anacardic acid) indicating greater quality fibers in treated plants.

Fiber fineness was calculated from fibers collected from the five plants each of the control and formulation treated in three replicates by HVI testing as micronaire and plotted by taking average (FIG. 6 and Table 2C). Similarly, fiber strength was calculated from fibers collected from the five plants each of the control and formulation treated in three replicates by HVI testing as gram/tex and plotted by taking average (FIG. 7 and Table 2D). Fiber yield (boll weight) was found to be higher and quality (fiber length, strength and fineness) was found to be better in case of ovules cultured with formulation (1-NAA+GA3-1-Anacardic acid) in comparison to control (Phytohormones only).

BIOLOGICAL EXAMPLES

The invention is to be illustrated by the biological examples, which follow, but without restricting it thereto.

Example 1

In-Vitro Cotton Ovule Culture Assay Using Appropriate Concentration of Anacardic Acid, 1-NAA and GA3

A) Cotton Ovule Culture

For standardization of appropriate concentrations of phytohormones and Anacardic acid for better yield and quality of fiber, the formulation and its components were first tested on cultured ovules. Liquid media was used for the ovule culture. The culture media contains ½ Murashige and Skoog liquid media (Murashige T and Skoog F, 1962. Physiol Plant 15: 473497) with 2% sucrose and 10 mg per liter L-cysteine. Culture media was poured in 35 mm cell culture dishes. On average 3-5 ovules were placed in to a single disc with 4 mL media, sealed with parafilm and kept at incubator for culture as per standard protocol (Beasley and Ting, 1973. Amer J Bot, 60: 130-139).

B) Standardization of Concentrations of Different Compounds (1-NAA, GA3 and Anacardic Acid) in the Formulation Cotton buds and flowers at −3 DPA and 1 DPA stage were plucked from the plants for initiation and elongation stage respectively. Ovaries were surface sterilized using 1% Mercuric chloride solution and washed three times with MQ water. Ovules were excised using sterilized fine forceps and brushes. Isolated ovules (3-5) were transferred to culture media (with different concentrations of 1-NAA (1, 5, 10 and 20 µM) and GA3 (0.1, 0.5, 1 and 5 µM) placed in 35 mm tissue culture dishes). These dishes were further placed in incubators set at two different temperatures 30° and 32° C. It has been observed that growth in cultures with 5 µM 1-NAA and 0.5 µM GA3 at 32° C. was better in comparison to other phytohormonal and temperature conditions. Similarly, different concentrations of Anacardic acid (2, 4, 8 and 10 µM) were also used and established that fiber growth was better at 8 µM Anacardic acid in media in comparison to other concentrations.

C) In-Vitro Ovule Culture Using Plant Growth Stimulating Formulation for Increase in Fiber Yield and Improvement in Fiber Quality.

Finally, in-vitro ovule culture experiment was performed with 8 µM Anacardic acid, 5 µM 1-NAA and 0.5 µM GA3 in media along with control sample having only 5 µM 1-NAA and 0.5 µM GA3. The phenotypic observations were recorded at 3 DPA for initiation stage and at 12 DPA for elongation stage (FIG. 1).

Example 2

Biochemical Quantification for Lignin in Control and Treated Cultured Ovules

Figure 2:
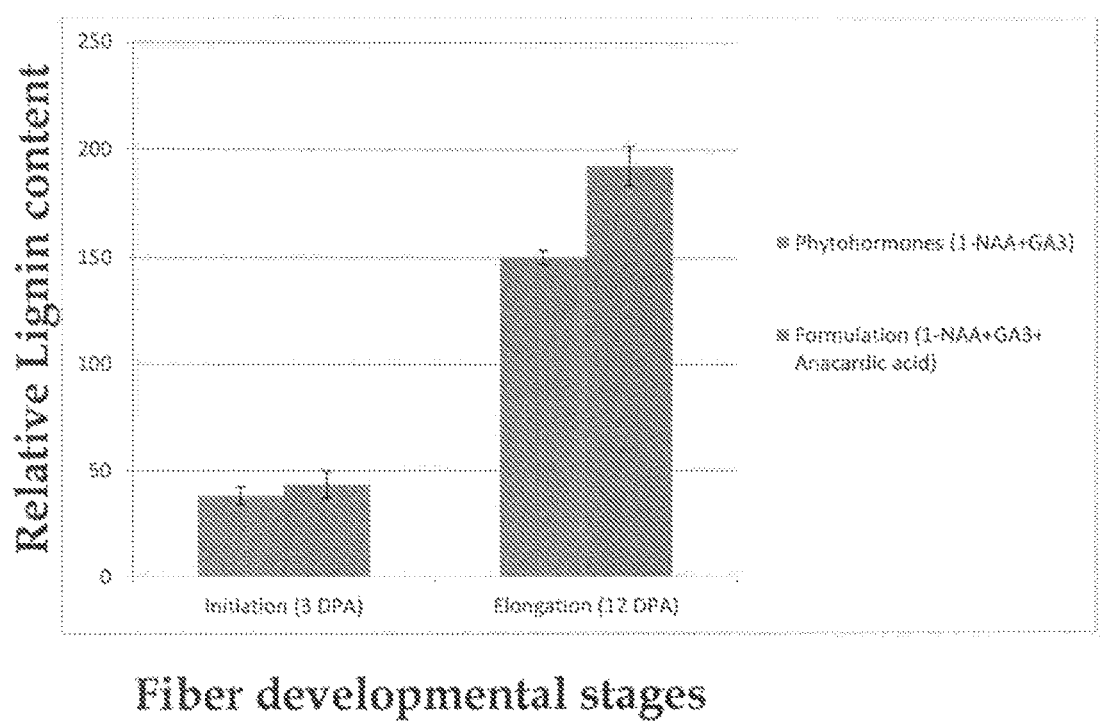
FIG. 2 illustrates the measurement of fiber quantity by lignin quantification of phytohormone (1-NAA+GA3) treated and formulation (1-NAA+GA3+ Anacardic acid) treated cultured ovules after initiation and at elongation stage. Measurement of relative lignin content is a very good method of comparing alterations in the length and number (yield) of the fibers. Lignin content was quantified by using Toluidine Blue solution (Beasley and Ting, 1974. American Journal of Botany. 61: 188-194). Lignin content is used as indirect measurement of cell growth or cell area. Cotton ovules cultured with Anacardic acid in culture media show higher lignin content in comparison to control ovules (without Anacardic acid) indicating higher yield in treated plants.

As lignin is present in the cell wall of the cotton fiber, measurement of relative lignin content is a very good method of comparing alterations in the length and number (yield) of the fibers. Quantification of lignin content in cells is the indirect method for measuring cell surface area (Al-Ghazi et al., 2009. Transcript profiling during fiber development identifies pathways in secondary metabolism and cell wall structure that may contribute to cotton fiber quality. Plant Cell and Physiology. 50(7): 1364-1381). Relative lignin content in the fibers collected from 3 cultured ovules for each sample (control and treated samples from initiation (at 3DPA) and elongation (at 12DPA) stage) was quantified using Toluidine Blue staining method (Beasley and Ting, 1974. Effects of plant growth substances on in vitro fiber development from unfertilized cotton ovules. American Journal of Botany. 61: 188-194). This method is based on quantitative spectrophotometric estimation of the binding of the dye Toluidine Blue to the cell surface of the fibers. Briefly, one locule was boiled in distilled water with a drop of concentrated HCl to dissolve waxes and leave the fibers hydrophilic. After rinsing in distilled water, three seeds were placed in a 50 ml falcon tube and stained with 30 ml of toluidine blue solution (0.018% toluidine blue, 0.016 M $Na_2HPO_4$, 0.01 M citric acid, pH 4.5) for 30 s. After staining, the seeds were rinsed thoroughly with distilled water and briefly laid on absorbent paper to remove excess water. Seeds were then returned to 50 ml falcon tubes and 50 ml of destaining solution comprising glacial acetic acid, ethanol and water (10:95:5) added. After vigorous shaking and destaining for at least 1 h, 200 µl of the solution was pipetted in triplicate into 96-well flat bottom microtiter plates for measurement of absorbance at 624 nm in a plate reader (FIG. 2 and Table 1). Lignin content was found to be higher in case of ovules cultured with formulation (1-NAA+ GA3+ Anacardic acid) in comparison to control (Phytohormones only).

TABLE 1

Biochemical quantification for lignin in control (phytohormone treated) and formulation (phytohormones + Anacardic acid) treated cultured ovules

| Treatment | Relative Lignin Content | |
|---|---|---|
| | Initiation (3 DPA) | Elongation (12 DPA) |
| 1. Phytohormones (1-NAA + GA3) | 38.26 ± 4.03 | 150.37 ± 6.3 |
| 2. Formulation (1-NAA + GA3 + Anacardic acid) | 43.54 ± 3.38 | 192.47 ± 9.1 |

Example 3

Field Trial of Anacardic Acid and Phytohormonal Formulation for its Effect on Cotton Fiber Yield and Quality by Direct Spray Method

*Gossypium hirsutum* genotypes were selected for testing the Anacardic acid and phytohormonal formulation for its effect on fiber yield and quality under normal agricultural practices. Seventy *Gossypium hirsutum* plants in 3 replicates each for control and formulation treatment (total 210 plants per treatment) were arranged in a Randomized Block Design. These plants were treated with the control (phytohormone only) and the formulation (1-NAA+GA3+ Anacardic acid). Anacardic acid, 1-NAA and GA3 were mixed with sterile water to a final concentration of 8 µM, 5 µM and 0.5 µM respectively. The aqueous solution was sprayed directly on to the flowering parts (buds, flowers and bolls) of the plants 3 to 5 times. Flowers were marked by tagging and bursted bolls were collected on maturity for testing of different yield and fiber parameters (FIGS. 4, 5, 6, 7 and Table 2). Fiber yield (boll weight) and quality (fiber length, strength and fineness) was found to be higher in case of plants treated with formulation (1-NAA+GA3+ Anacardic acid) in comparison to control (Phytohormones only).

TABLE 2

Yield and fiber quality parameters in fiber from control (phytohormone treated) and formulation (phytohormones + Anacardic acid) treated plants.

| Parameters | Phytohormones (1-NAA + GA3) | Formulation (1-NAA + GA3 + Anacardic acid) |
|---|---|---|
| A. Boll weight (grams) | 6.21 | 7.1* |
| B. Fiber length (mm) | 29.4 | 30.7** |
| C. Fiber fineness (micronaire) | 3.99 | 3.66** |
| D. Fiber strength (gram/tex) | 21.27 | 22.38* |

**Significant with p-value 0.01;
*Significant with p-value 0.05;

Statistical significance was calculated by applying "t-test" statistics (one-tailed test for two-samples with unequal variance) on the data. All the three replicates of Control and treatment were considered for the analysis.

Example 4

Standardization of different phytohormones (1-NAA, GA3, IAA,2,4-D, Kinetin, and Zeatin) in the formulation To check the effect of the phytohormones on fiber development for better yield and quality of fibers, different phytohormones and their combinations were tested first tested on cultured ovules. Cotton buds and flowers at 1 DPA stage were plucked from the plants for the ovule culture. Ovaries were surface sterilized using 1% Mercuric chloride solution and washed three times with MQ water. Ovules were excised using sterilized fine forceps and brushes. Isolted ovules (3-5) were transferred to culture media with different 5 µM of 1-Naphthaleneacetic acid (1NAA), Indole-3-acetic acid (IAA), 2,4-Dichlorophenoxyacetic acid (2,4-D), Kinetin, Zeatin and 0.5 µM Gibberellic acid (GA3)along with untreated ovules (having no phytohormones) placed in 35mm tissue culture dishes in two sets. All the dishes were further places in incubators set at 32° C. In one set of dishes, Anacardic acid was added to 3 DPA stage, while the other set was used to control. It has been observed that at 12 DPA stage growth in cultures having Anacardic acid with phytohormones like 1-NAA, IAA, 2,4-D and GA3 at 3220 C. was better in comparison to the control conditions, where only phytohormones were used (FIG. 8). These results were also validated by qualification of lignin content (FIG.9). For the lignin qualification, ovules were boiled in distilled water with a drop of concentrated HCl to dissolve waxes and leave the fibers hydrophilic. After rinsing in distilled water, three ovules per sample were places in a 50 ml falcon tube and stained with 30 ml. of toluidine blue solution (0.018% toluidine blue, 0.016 M $Na_2HPO_4$, 0.01 M citric acid, pH 4.5) for 30 s. After staining, the ovules were rinsed thoroughly with distilled water and briefly laid on absorbent paper to remove excess water. Ovules were then returned to 50 ml falcon tubes and 50 ml of destaining solution comprising glacial acetic acid, ethanol and water (10:95:5) added. After vigorous shaking and destaining for at least 1 h, 200µl of the solution was pipetted in triplicate into 96-well flat bottom microtiter plates for measurement of absorbance at 624 nm in a plate reader. Lignin content was found to be higher (FIG. 9) in case of ovules cultured with Anacardic acid and phytohormones like 1-NAA, IAA, 2,4-D and GA3 (1-NAA +GA3+Anacardic acid) in comparison to control wherein only phytohormones are used.a2

The invention claimed is:

1. A plant growth stimulating formulation, suitable for improving fiber yield and quality of the plant, comprising a solution of Anacardic acid or its other derivatives at a concentration ranging from 2-20µM, along with Phytohormone ingredients 1-Naphthaleneacetic acid (1-NAA), and Gibberellic Acid; wherein the presence of anacardic acid or its other derivatives in the formulation in combination with the phytohormone ingredients improves the fiber yield and quality of the plant.

2. A plant growth stimulating formulation as claimed in claim 1, wherein the solvent used
for Anacardic Acid is selected from dimethyl sulfoxide (DMSO), dimethyl formamide (DMFO), ethanol methanol, dichloromethane, ether, petroleum ether and ethyl acetate in a biologically effective concentration.

3. A plant growth stimulating formulation as claimed in claim 1, wherein the solvent used
for Anacardic acid or its derivatives is dimethyl sulfoxide (DMSO).

4. A plant growth stimulating formulation as claimed in claim 1, wherein the concentration of 1-NAA used in the formulation is in the range of 2 to 20 µM.

5. A plant growth stimulating formulation as claimed in claim 1, wherein the concentration of GA3 or gibberellic acid used in the formulation is ranging from 0.1 to 5 µM.

6. A plant growth stimulating formulation as claimed in claim 1, wherein the formulation contains 27.84 mg/litre Anacardic acid, 1.12 mg/litre 1-NAA and 0.173 mg/litre GA3.

7. A plant growth stimulating formulation as claimed in claim 1, wherein the formulation is formulated into a liquid, paste, powder or granule composition.

8. A method of application of plant growth stimulating formulation as claimed in claim 1 to a cotton plant useful for improvement in yield and quality of cotton fiber in the cotton plant.

9. A plant growth stimulating formulation as claimed in claim 1, wherein application of the formulation to cotton plants increases boll weight approximately by 1.8% to 29.39%.

10. A plant growth stimulating formulation as claimed in claim 1, wherein application of the formulation to cotton plants increases fiber length approximately by 0.57% to 11.09%.

11. A method of enhancing the yield and quality of cotton fiber using the formulation as claimed in claim 1 comprising the steps of
(a) spraying of the formulation on the shoot or buds, flowers and bolls of the cotton plant; alternatively, top dressing of the formulation on the cotton plants if the formulation is in powder or granule form;
(b) repeating the process for 3-5 times;
(c) setting a desired yield on maturity of seeds of sprayed flower, buds and bolls.

* * * * *